United States Patent [19]
Das et al.

[11] Patent Number: 5,869,708
[45] Date of Patent: Feb. 9, 1999

[54] PROCESS FOR THE ISOLATION OF ORYZANOLS FROM CRUDE DARK ACID OIL (RICE BRAN)

[76] Inventors: Prashanta Kumar Das; Arabinda Chaudhuri; Thengumpillil Narayana Balagopala Kaimal; Uday Triambakaraj Bhalerao, all of Hyderabad 500 007, Andra Pradesh, India

[21] Appl. No.: 785,357

[22] Filed: Jan. 17, 1997

[51] Int. Cl.$^6$ ........................................ C07J 53/00
[52] U.S. Cl. ............................................. 552/510
[58] Field of Search ............................... 552/510

Primary Examiner—Jose G. Dees
Assistant Examiner—Alton Pryor
Attorney, Agent, or Firm—Rines and Rines

[57] ABSTRACT

A process for the isolation of oryzanols from crude dark acid oil (rice bran) which comprises (a) distilling the free fatty acids from crude dark acid oil by conventional methods, (b) hydrolyzing the resultant residue by conventional methods, (c) dissolving the hydrolyzed product in water to form oryzanol containing micellar aggregates and adding dropwise aqueous solution of calcium chloride to form precipitate, (d) extracting the oryzanols from dried precipitate with polar organic solvent and if desired (e) purifying the oryzanols from the organic extract by column chromatography.

5 Claims, No Drawings

PROCESS FOR THE ISOLATION OF ORYZANOLS FROM CRUDE DARK ACID OIL (RICE BRAN)

This invention relates to an improved process for the isolation of oryzanols from crude dark acid oil (Rice Bran). Oryzanols are mixtures containing ferulate (4-hydroxy-3-methoxy cinnamic acid) esters of triterpene alcohols and plant sterols. Recent investigations have unequivocally demonstrated the multitude of beneficial physiological effects associated with oryzanol intake. The hypocholesterolemic activity of rice bran oil has been shown to be due to its constituent oryzanol and to some other components of the unsaponifiable matter [Seetharamaiah, G. S. and Chandrasekhara, N. Atherasclerosis: 78.219 (1989)]. Lipid peroxidation has been shown to be prevented in the retina by gamma-oryzanol because of its antioxidant property [Heramitsu, Tadahisa and Armstrong Donald, Opthalmic Res: 23, 196 (1991)]. Pharmaceutical preparations containing oryzanols have been shown to successfully reduce wrinkles in aged women [Sakai, Tatsu et al (Eisai Co. Ltd.); JP 05.30.526 (1993)]. Melanin formation accelerating topical preparations containing 1 weight % oryzanol have been shown to convert gray hair into natural black [Sakai, Tatsu et al (Eisai Co. Ltd.); JP 05.225.037 (1993)]. Nail lacquers containing oryzanols prevent discoloration of nails [Ito, Nobumasa (Pola Chemical Industries Inc.), JP 02.290.806 (1990)]. Deodorant formulations containing oryzanols are especially effective in controlling odor from perspiration and underarms [Kumasaka, Sadao (Human Industry Corp.): JP 633322 (1988)]. Oryzanol containing pharmaceutical formulations are used in preventing motion sickness [Sakada, Hideharu; JP 82.32.229 (1982)] and in the treatment of nervous system disorder [Sun. Zhide and Cong Yizi; CN 87,101,519 (1988)]. A plethora or oryzanol containing transdermal pharmaceutical and moisturizing cosmetic preparations have been prepared for the treatment of skin disorders [Courtin, Olivier (Clarins S. A.), FR 2,688,137 (1993); Tokuda, Yasuaki et al (Nissei Marine Kogyo K.K.). JP 01,290,613 (1989); Ichimaru Co. Ltd., Orizu Yuka Co. Ltd., JP 81,161,315 (1981); Toyo Chemical Corp. JP 82,149,212 (1982); Zenyaku Kogyo Co. Ltd., JP 82,42,621 (1982); Nitto Electric Industrial Co. Ltd., JP 59,53,415 (1984), JP 59,184,120 (1984)]. Oryzanol emulsions are used as antioxidants and preservatives for cosmetics & foods and such emulsions are also effective in preventing color changes in the products. [Orita Yuka Co. Ltd., JP 58,45,728 (1983)]. Soft capsules containing oryzanols with or without riboflavin butyrate can be used to prevent arteriosclerosis [Nisshin Kogaku K.K. JP 58,103,315 (1983)]. Bath preparations containing 3–20% (by weight) oryzanols are used in treatment of atopic dermatitis and senile xeroderma [Inoe, Toshio and Nunokawa Senzo (Otsuka Pharm Co. Ltd.; JP 05,279, 272 (1993)]. Oryzanols have been shown to be highly effective against lipogenic liver cirrhosis in spontaneously hypertensive rats, an animal having natural abnormalism in lipid metabolism [Ito, Masahiro et al; J. Clin Biochem. Nutr. 12,193 (1992)]. Investigations directed towards the safety assessment of oryzanols clearly indicate that oryzanols possess no genotoxic and carcinogenic initiation activities [Tsushimoto. Gen et al, J. Toxicol. Sci. 16,191 (1991); Tamagawa, M et al. Food. Chem. Toxicol. 30.49. (1992)]. All these remarkable beneficial effects of oryzanols on human health have generated, in recent years, an upsurge of global interest in developing commercially viable methods for the isolation of oryzanols from its various natural sources.

Rice bran oil is perhaps the most readily accessible source for the isolation of oryzanol. The oryzanol content of rice bran oil varies within the range of 1.1 to 2.6%. The soap stock obtained by alkali refining of rice bran oil contains 1.3–3.1% oryzanol. Oryzanols were first isolated from rice bran oil [Kaneko, R. and T. Tsuchiya; J. Chem Soc. Jpn. 57,526(1954); Tsuchiya, T. et al; JP 4895 (1957)] was presumed to be a single component. Later is was determined to be a mixture containing ferulate (4-hydroxy-3-methoxy cinnamic acid) esters of triterpene alcohols and plant sterols. Individual components were identified as ferulate esters of cycloartenol, 24-methylene-cycloartanol, campesterol, beta-sitosterol and other sterols. Over the decades, the methods of oryzanol isolation from plant oils have been improved. Such methods include isolation of cycloartanol ferulate from plant oil using selective organic solvent for oryzanol extraction followed by chromatographic purification [Kimura, Goro, Jap Pat 6314796 (1988) & Jap Pat 6314797 (1988)], isolation of oryzanols from rice bran dark oil by precipitating the stearins with aluminium sulfate followed by crystallization of oryzanols from the supernatant [Beso oils & Fats Co. Ltd., Jap Pat 8295942 (1982)], highly concentrated separation of oryzanols from rice bran and rice germ oils by two-step alkali treatment [Shimuzu, Hisashi; Jap Pat 76123811 (1976)], extraction of oryzanols from rice bran soapstock with diethylether at pH 9.5 followed by its chromatographic purification on a neutral alumina column [G. S. Seetharamaiah and J. V. Prabhakar; J. Food Science Technology, 23,270 (1986)], extraction of oryzanols from rice bran oil soap stock with ether after acidification of soap stock with HCl [Tomotaro, Tsuchiya et al; Jap Pat 4895 (1957)], isolation of oryzanols by transesterification of rice bran dark oil with methanol and sulfuric acid followed by column chromatography over pretreated Amberlite IRA-401 using mixed solvent methanol and ether as the eluent [Tomaro, Tsuchiya and Osamu, Okubo; Jap Pat 13649 (1961)], isolation of 98.3% pure oryzanols in overall about 35% yield by liquid-liquid extraction of hexane solution of 20.2% concentrated solution of oryzanol using water-saturated furfural as the extractant [Watanabe, Yasuo et al; Jap Pat 6812731 (1968)], isolation of 85% pure oryzanols by passing carbon dioxide gas through a methanolic solution of alkaline oil cake of rice bran oil [Nishihara, Masao and Shibuya, Yoshizane; Jap Pat 7812730 (1968)] and extraction of oryzanols from the raw oils of rice bran and ferment, maize & barley by distillation of these oils at comparatively low temperature followed by extracting the residue with hydroxol solvents [Yamamoto, Takeshi, Ger Pat 1301002 (1969). During rice bran oil refining, a significant amount of rice bran oil gets trapped within the soap that is formed in the deacidification step. When the soap is removed by centrifugation, the entrapped oil also gets centrifuged with the soap. The centrifuged oil and soap is called soapstock. Soap industries use these soap stocks as their principal raw materials for manufacturing their bath preparations and toiletries. The soap stock is reacidified to prepare crude dark acid oil. The pure free fatty acids are distilled out from the crude dark acid oil under high vacuum. The entrapped oryzanols of soap stock is left in the residue, the so-called pitch, after the removal of free fatty acids from the crude dark acid oil. Thus it would be a plus to the arsenal of the oryzanol isolation methods if a commercially viable technology is developed for the isolation of oryzanol from the residue of crude dark acid oil after the distillation of free fatty acids under high vacuum.

The main object of the present invention is therefore to provide a process for the isolation of oryzanols from the residue of crude dark acid oil after distilling off the free fatty acids under vacuum. Accordingly, the present invention provides an improved process for the isolation of oryzanol from the residue of crude dark acid oil which comprises (a) distilling the free fatty acids from crude dark acid oil by conventional methods, (b) hydrolyzing the resultant residue by conventional methods, (c) dissolving the hydrolyzed product mixture in predetermined amount of water to form oryzanol containing micellar aggregates, (d) adding dropwise aqueous solution of calcium chloride to form precipitate and extracting the oryzanol from the dried precipitate with polar organic solvent, and if desired (e) purifying the oryzanol from the organic extract by column chromatography.

By the process of the present invention, a major part of the oryzanol that survives the vacuum distillation step for the free fatty acid removal, can be isolated in highly pure form. The byproducts are the calcium salts of various long chain fatty acids (mainly palmitic, stearic, oleic and linoleic acids) which can be utilized for various industrial applications. The invention accordingly provides a micellar chemistry based isolation of oryzanols from the crude dark acid oil.

Micelles are roughly spherical aggregates of surfactant molecules in water. Such aqueous micellar aggregates can solubilize, in their hydrocarbon like interior, various hydrophobic molecules which are otherwise highly insoluble in water. Solubility of the ionic micelles in water can be drastically reduced by exchanging the counterions. In the present invention, the residue after distilling off the free fatty acids under high vacuum is hydrolyzed with aqueous sodium hydroxide solution at a temperature in the range of 60° to 90° C. for 0.5 to 4 hours and the hydrolyzed product mixture is dissolved in excess water to form oryzanol containing anionic micelles. For such anionic micelles of sodium salts of long chain fatty acids, addition of calcium ions induces immediate aggregation of the oryzanol containing micelles causing them to precipitate from water. The precipitate is then dried, extracted with polar organic solvent like ethyl acetate, chloroform and methanol. The organic extract is then washed with dilute aqueous alkali followed by water, dried over anhydrous sodium sulfate and the dried extract is evaporated. The oryzanol is finally purified from the residue by column chromatography using silica gel column and chloroform as eluent.

The details of the invention is further illustrated with the following examples which should not be however, be construed to limit the scope of the invention.

EXAMPLE 1

About 61 g of commercial dark acid oil containing 50–60% free fatty acids was distilled at 250° C.–260° C. under high vacuum (1 mm Hg) for removing most of its free fatty acids. The weight of the residue after distilling off the free fatty acids was about 34 g and its free fatty acid content was determined to be about 10%. About 11 g of this residue was hydrolyzed with aqueous sodium hydroxide (1.8 g NaOH in 25 ml water) at 80°–90° C. for 3 hr. The hydrolyzed product mixture turned to a dark brown and somewhat viscous homogeneous solution. About 200 ml distilled water was added to this hydrolyzed product mixture, stirred at room temperature for about 30 min and to the solution, while being stirred, an aqueous solution of calcium chloride (2.5 g $CaCl_2$ dissolved in 30 ml. distilled water) was added dropwise. A huge precipitate appeared and the mixture was kept under stirring condition for another 15 minutes. The precipitate was then filtered and air dried, the dried precipitate was extracted with 100 ml. ethyl acetate by stirring at 50° C. for 30 min. centrifuged (5000 rpm) at 15° C. and the supernatant was saved. This extraction protocol was repeated two times with the centrifuged precipitate. The combined ethylacetate extracts was then washed with 5% aqueous alkali (3×100 ml) and then with water (3×100 ml) and dried over anhydrous sodium sulfate. Ethyl acetate was evaporated off using a rotatory evaporator and finally the oryzanols were purified from the residue by silica gel column chromatography using a 3.2×25 cm column and pure chloroform as the eluent. The oryzanol containing fractions (the volume of each collected fraction was about 10 ml) were combined and chloroform was evaporated. At this state, after removal of chloroform, the residue (almost white in appearance) was further purified by activated charcoal (<1%) treatment in hot methanol solution. The filtrate, on overnight cooling, gave perfect white oryzanols crystals (320 mg). The recovery of oryzanols based on the maximum literature value of total oryzanol content (3%) [G. S. Seetharamaiah and J. V. Prabhakar; J. Food Science Technology, 23,270 (1986)] of the starting crude dark acid oil was about 54%. The UV spectra of the isolated oryzanol in chloroform was found to be practically superimposable with the published spectra (Observed $\lambda$ max values: 319 mn, 294.4 nm & 243.4 nm) [E. J. Rogers et al, J. Am. Oil Chem. Soc. 70,301 (1993)] and quantitative UV spectrophometric analysis indicated the purity level of the isolated oryzanol to be about 85%. The melting point of the isolated oryzanol sample was determined to be within the range of 120°–125° C. The Reverse phase C-18 (Water's millipore column) HPLC of the purified oryzanols showed the presence of all the four components (with the same retention times) those are present in a commercially available oryzanol samples. The observed retention times are 13.08 min. 14.42 min. 16.23 min. and 18.69 mins. The mobile phase consisted of acetonitrile/methanol/isopropanol (50:45:5 vol/vol/vol). The LC system used was of Shimadzu with 20 $\mu$l sample loop. Oryzanol components were detected at 325 nm following a published protocol (E. J. Rogers et al. J. Am. Oil Chem. Soc. 70,301 (1993)].

EXAMPLE 2

About 10.2 g of the residue, obtained after removal of the free fatty acid from crude dark acid oil, was hydrolyzed with aqueous sodium hydroxide (1.7 g NaOH in 25 ml water) at 80°–90° C. for ½ hr. The hydrolyzed product mixture turned to a dark brown and somewhat viscous homogeneous solution. About 200 ml distilled water was added to this hydrolyzed product mixture, stirred at room temperature for about 30 min and to the solution, while being stirred, an aqueous solution of calcium chloride (2.3 g $CaCl_2$ dissolved in 30 ml. distilled water) was added dropwise. A huge precipitate appeared and the mixture was kept under stirring condition for another 15 minutes. The precipitate was then filtered and air dried, the dried precipitate was extracted with 100 ml. ethyl acetate by stirring at 50° C. for 30 min, centrifuged (5000 rpm) at 15° C. and the supernatant was saved. This extraction protocol was repeated two times with the centrifuged precipitate. The combined ethyl acetate extracts was then washed with 5% aqueous alkali (3×100 ml) and then with water (3×100 ml) and dried over anhydrous sodium sulfate. Ethyl acetate was evaporated off using a rotatory evaporator and finally the oryzanols were purified from the residue by silica gel column chromatography using a 3.2×25 cm column and pure chloroform as the eluent. The oryzanol containing fractions (the volume of each collected fraction was about 10 ml) were combined and chloroform was evaporated. At this state, after removal of chloroform, the residue (almost white in appearance) was further purified by activated charcoal (<1%) treatment in hot methanol solution. The filtrate, on overnight cooling, gave perfect white oryzanols crystals (362 mg). The recovery of oryzanols based on the maximum literature value of total oryzanol content (3%) [G. S. Seetharamaiah and J. V. Prabhakar; J. Food Science Technology, 23,270 (1986)] of the starting crude dark acid oil was 66%. The quantitative UV spectrophometric analysis indicated the purity level of the isolated oryzanol to be about 85%. The melting point of the isolated oryzanol sample was determined to be within the range of 120°–125° C.

EXAMPLE 3

About 11 g of the residue, obtained after removal of the free fatty acid from crude dark acid oil, was hydrolyzed with aqueous sodium hydroxide (1.8 g NaOH in 25 ml water) at 80°–90° C. for 1 hr. The hydrolyzed product mixture turned to a dark brown and somewhat viscous homogeneous solution. About 200 ml distilled water was added to this hydrolyzed product mixture, stirred at room temperature for about 30 min and to the solution, while being stirred, an aqueous solution of calcium chloride (2.5 g $CaCl_2$ dissolved in 30 ml. distilled water) was added dropwise. A huge precipitate appeared and the mixture was kept under stirring condition for another 15 minutes. The precipitate was then filtered and air dried, the dried precipitate was extracted with 100 ml. ethyl acetate by stirring at 50° C. for 30 min. centrigured (5000 rpm) at 15° C. and the supernatant was saved. This extraction protocol was repeated two times with the centrifuged precipitate. The combined ethyl acetate extracts was then washed with 5% aqueous alkali (3×100 ml) and then with water (3×100 ml) and dried over anhydrous sodium sulfate. Ethyl acetate was evaporated off using a rotatory evaporator and finally the oryzanols were purified from the residue by silica gel column chromatography using: 3.2×25 cm column and pure chloroform as the eluent. The oryzanol containing fractions (the volume of each collected fraction was about 10 ml) were combined and chloroform was evaporated. At this state, after removal of chloroform, the residue (almost white in appearance) was further purified by activated charcoal (<1%) treatment in hot methanol solution. The filtrate, on overnight cooling, gave perfect white oryzanols crystals (510 mg). The recovery of oryzanols based on the maximum literature value of total oryzanol content (3%) [G. S. Seetharamaiah and J. V. Prabhakar; J. Food Science Technology, 23,270 (1986)] of the starting crude dark acid oil was about 86%. Quantitative UV spectrophomeric analysis indicated the purity level of the isolated oryzanol to be about 85%. The melting point of the isolated oryzanol sample was determined to be within the range of 120°–125° C.

Advantages of the present invention:

1. The process can recover highly pure oryzanols from dense dark brown pitchlike byproducts of rice bran oil processing industries.
2. Recovery of oryzanol is quite high.
3. The byproducts calcium soaps (mainly calcium oleate, calcium palmitate and calcium sterate) can be utilized by industries manufacturing water proofing fabrics, cements, releasing agents for plastic molding powder, stabilizers for polyvinyl chloride resins, lubricants, conditioning agents in pharmaceutical products etc.

We claim:

1. In a process for effecting production of oryzanols from crude dark acid oil as of rice bran, the improvement comprising the steps of (a) distilling the free fatty acids from the crude dark acid oil;

(b) hydrolyzing the resultant residue;

(c) dissolving the hydrolyzed product in water of amount predetermined for micellar aggregate formation in oryzanol thereby to form oryzanol containing micellar aggregates and adding dropwise aqueous solution of calcium chloride to form a precipitate;

(d) drying the precipitate; and (e) extracting the oryzanols from the dried precipitate with polar organic solvent.

2. The process as claimed in claim 1, wherein the hydrolysis is carried out using aqueous sodium hydroxide solution at a temperature in the range of 60°–90° C. for a period in the range of 0.5–4 hours.

3. The process as claimed in claim 1, wherein the polar organic solvent used is selected from the group consisting of ethyl acetate, chloroform and methanol.

4. The process as claimed in claim 1, wherein the oryzanols are purified from the organic extract by column chromatography.

5. The process as claimed in claim 4, wherein purification of oryzanols is effected by silica gel column chromatography using polar organic eluents selected from the group consisting of chloroform, ethylacetate/hexane and chloroform/methanol.

* * * * *